(12) United States Patent
Walker et al.

(10) Patent No.: US 11,261,987 B2
(45) Date of Patent: Mar. 1, 2022

(54) ROTARY VALVE

(71) Applicant: Medical Instrument Development Laboratories, Inc., San Leandro, CA (US)

(72) Inventors: Jeffrey Allen Walker, Livermore, CA (US); Erik William Peterson, Walnut Creek, CA (US)

(73) Assignee: MEDICAL INSTRUMENT DEVELOPMENT LABORATORIES, INC., San Leandro, CA (US)

( * ) Notice: Subject to any disclaimer, the term of this patent is extended or adjusted under 35 U.S.C. 154(b) by 115 days.

(21) Appl. No.: 16/795,215

(22) Filed: Feb. 19, 2020

(65) Prior Publication Data
US 2021/0254744 A1    Aug. 19, 2021

(51) Int. Cl.
| | | |
|---|---|---|
| F16K 31/04 | (2006.01) | |
| F16K 27/08 | (2006.01) | |
| A61B 17/14 | (2006.01) | |
| A61B 17/00 | (2006.01) | |

(52) U.S. Cl.
CPC .......... *F16K 31/043* (2013.01); *A61B 17/142* (2016.11); *F16K 27/08* (2013.01); *A61B 2017/00544* (2013.01)

(58) Field of Classification Search
CPC ..... Y10T 137/86662; Y10T 137/86871; Y10T 137/87708; Y10T 137/87772; Y10T 137/87909; Y10T 137/8782; Y10T 137/86863; F16K 11/085; F16K 11/0856; F16K 31/04; F16K 31/041; F16K 31/043; F16K 31/046; A61B 17/142; A61B 17/144; A61B 17/1628; A61B 2017/00544; B25D 9/08

USPC ..... 251/207–209, 129.11, 310, 311; 173/201
See application file for complete search history.

(56) References Cited

U.S. PATENT DOCUMENTS

| | | | |
|---|---|---|---|
| 1,024,909 A | | 4/1912 | Powelsen |
| 1,059,485 A | * | 4/1913 | Orlopp ...................... F01L 7/16 123/190.8 |
| 2,371,657 A | * | 3/1945 | Stark ...................... F16K 11/085 251/182 |

(Continued)

FOREIGN PATENT DOCUMENTS

CN        106640326 A       5/2017

OTHER PUBLICATIONS

International Search Report and Written Opinion for Application No. PCT/US2021/018342 dated May 4, 2021 (13 pages).

*Primary Examiner* — Matthew W Jellett
(74) *Attorney, Agent, or Firm* — Michael Best & Friedrich LLP

(57) ABSTRACT

A rotary valve includes a rotor housing having a first centrally-located aperture extending axially through the rotor housing, an inlet port, and an outlet port. The inlet port and the outlet port each extend radially and open into the first centrally-located aperture. The rotary valve further includes a rotor to be disposed within the first centrally-located aperture. The rotor includes a main body and a dwell space extending radially inwardly into the main body and circumferentially around a portion of the main body. The rotor further includes a second centrally-located aperture that extends axially through a distal end of the rotor and into the dwell space within the main body.

29 Claims, 12 Drawing Sheets

(56) References Cited

U.S. PATENT DOCUMENTS

| | | | | |
|---|---|---|---|---|
| 2,860,660 A * | 11/1958 | Swatsworth | ............ | F16K 31/56 |
| | | | | 137/625.42 |
| 3,465,835 A * | 9/1969 | Krivit | ................. | A61B 17/92 |
| | | | | 173/170 |
| 3,558,100 A | 1/1971 | Hulsey | | |
| 4,203,444 A | 5/1980 | Bonnell et al. | | |
| 4,345,622 A | 8/1982 | Henningsson | | |
| 4,449,550 A * | 5/1984 | Ranalli | ............ | A61F 9/00763 |
| | | | | 137/624.13 |
| 4,480,662 A | 11/1984 | Garrels | | |
| 4,649,955 A * | 3/1987 | Otto | ................ | F16K 3/34 |
| | | | | 137/625.13 |
| 4,802,508 A * | 2/1989 | Styles | ................ | A47K 5/1217 |
| | | | | 134/199 |
| 4,881,574 A * | 11/1989 | Olson | ................ | G21C 19/46 |
| | | | | 137/624.13 |
| 4,944,261 A | 7/1990 | Coates | | |
| 4,953,595 A * | 9/1990 | Kotlyar | ................ | E21B 21/10 |
| | | | | 137/624.13 |
| 5,143,121 A * | 9/1992 | Steinhardt | ............ | E03C 1/0408 |
| | | | | 137/597 |
| 5,242,150 A | 9/1993 | Shiffler et al. | | |
| 5,584,322 A | 12/1996 | Pöschl et al. | | |
| 6,436,067 B1 | 8/2002 | Deng et al. | | |
| 6,868,859 B2 * | 3/2005 | Yudovsky | ............. | F16K 11/074 |
| | | | | 137/1 |
| 6,962,169 B2 * | 11/2005 | Kaske | ................. | B01D 29/114 |
| | | | | 137/624.13 |
| 7,322,375 B2 | 1/2008 | Goldfarb et al. | | |
| 7,377,291 B2 | 5/2008 | Moon et al. | | |
| 7,690,397 B2 * | 4/2010 | Hollis | .................. | F16K 11/076 |
| | | | | 137/625.47 |
| 8,166,992 B2 * | 5/2012 | Samaroo | ............... | B09C 1/002 |
| | | | | 137/1 |
| 8,475,481 B2 | 7/2013 | Himes | | |
| 8,500,620 B2 | 8/2013 | Lu et al. | | |
| 8,661,782 B2 * | 3/2014 | Kenyon | ................ | F02C 5/10 |
| | | | | 60/247 |
| 9,567,894 B2 | 2/2017 | Oikawa et al. | | |
| 10,383,766 B2 * | 8/2019 | Farley | ................. | A61M 39/227 |
| 2009/0223657 A1 | 9/2009 | Hollis | | |
| 2010/0191106 A1 | 7/2010 | Koyama | | |
| 2014/0171995 A1 | 6/2014 | McDonell | | |
| 2014/0276369 A1 | 9/2014 | Banko | | |
| 2015/0032139 A1 | 1/2015 | Sjostrom | | |
| 2016/0223090 A1 | 8/2016 | G.R. | | |

\* cited by examiner

ROTARY VALVE

BACKGROUND

A variety of medical cutting instruments exist. One type of medical cutting instrument includes a reciprocating cutter that is operated pneumatically with compressed air. Some instruments, for example, supply the compressed air to a diaphragm within the instrument to generate the reciprocating action of the cutter. A valve is sometimes used to pulse the air as the air is delivered to the instrument. Traditional valves, however, are unable to create a high frequency pulse train necessary to achieve desired high cut rates.

SUMMARY

In accordance with one example construction, a rotary valve for a medical cutting instrument includes a rotor housing having a first centrally-located aperture extending axially through the rotor housing, an inlet port, and an outlet port. The inlet port and the outlet port each extend radially and open into the first centrally-located aperture. The rotary valve also includes a rotor to be disposed within the first centrally-located aperture. The rotor includes a main body and a dwell space extending radially inwardly into the main body and circumferentially around a portion of the main body. The rotor also includes a second centrally-located aperture that extends axially through a distal end of the rotor and into the dwell space within the main body.

Other embodiments and aspects of various embodiments will become apparent by consideration of the detailed description and accompanying drawings.

DETAILED DESCRIPTION

Before any embodiments are explained in detail, it is to be understood that embodiments are not limited in their application to the details of construction and the arrangement of components set forth in the following description or illustrated in the following drawings. Other embodiments are possible and embodiments described and illustrated are capable of being practiced or of being carried out in various ways.

Figure 1:
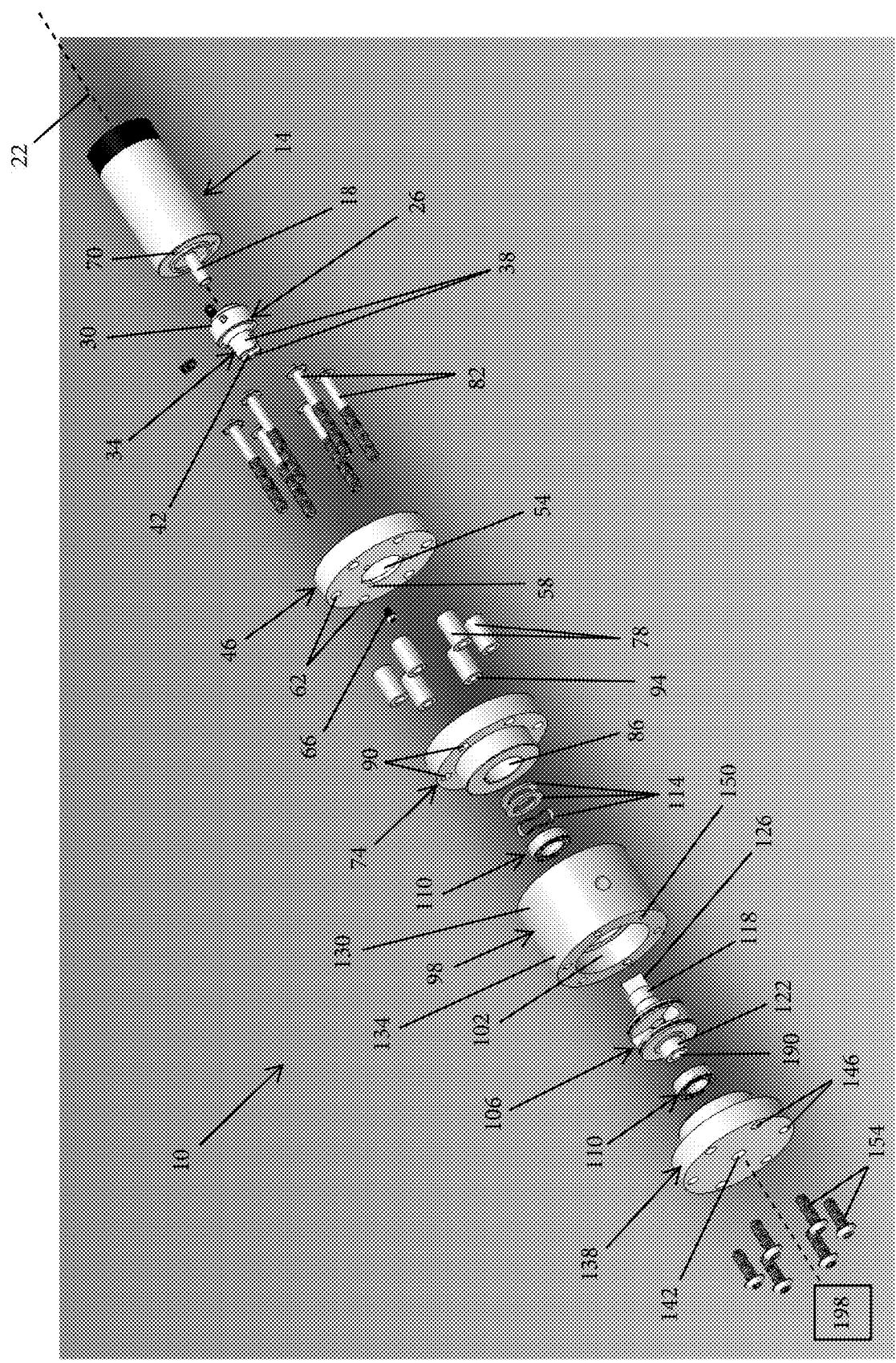
FIGS. 1 and 2 illustrate an exploded, perspective view of a rotary valve.
Figure 2:
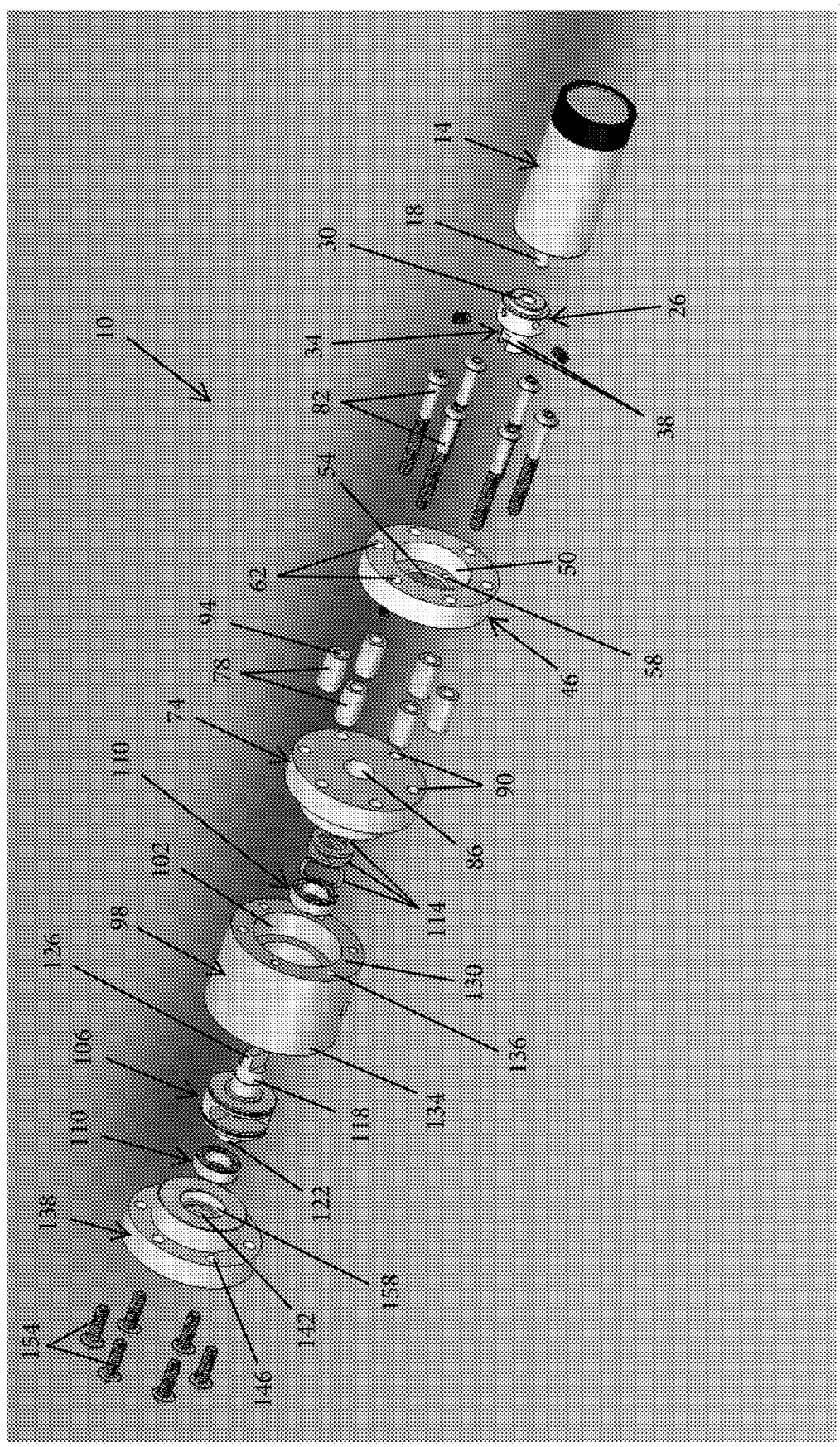

FIGS. 1 and 2 illustrate an example rotary valve 10. The rotary valve 10 is described in the context of being used with a medical cutting instrument, although the rotary valve 10 may be used with other instruments, including other medical instruments, to control a flow of compressed air or other fluid to an instrument.

In the illustrated example construction, the rotary valve 10 includes a motor 14. The motor 14 includes a drive shaft 18 that extends from one end of the motor 14 and rotates about a drive axis 22. The illustrated motor 14 is an electric motor, although other constructions include different types of motors 14. The drive shaft 18 has a rotational speed about the drive axis 22 that varies between 0-40,000 revolutions per minute (rpm), although other constructions include different rotational speeds other than 0-40,000 rpm (for example, motors with rotational speeds that extend higher than 40 k rpm).

With continued reference to FIGS. 1 and 2, the rotary valve 10 further includes a drive coupling 26 that couples to and rotates with the drive shaft 18. For example, the drive coupling 26 may be fixed at a proximal end 30 to the drive shaft 18 via threading or a fastener, or may be welded or integrally formed as a single piece with the drive shaft 18. In the illustrated example construction, the drive coupling 26 includes a distal end 34 that is located opposite the proximal end 30, and includes two protruding portions 38 that define a gap 42 therebetween. Other constructions include different shapes and sizes of a drive coupling 26 other than those illustrated. In some constructions, the drive coupling 26 includes fewer or more than two protruding portions 38, or does not include any protruding portions 38.

With continued reference to FIGS. 1 and 2, the rotary valve 10 also includes a motor mount 46 for mounting the motor 14. In the example illustrated, the motor mount 46 includes a cylindrically-shaped recessed region 50 (FIG. 2) along one side of the motor mount 46 that is sized and shaped to receive a portion of the motor 14. The motor mount 46 further includes a centrally-located aperture 54, inner mounting apertures 58 spaced circumferentially around the centrally-located aperture 54, and outer mounting apertures 62 spaced circumferentially around the centrally-located aperture 54. Other constructions include various shapes and sizes of a motor mount 46 other than those illustrated. Different numbers and arrangements of mounting apertures and/or recessed regions are also possible.

To mount the illustrated motor 14 to the motor mount 46, the motor 14 and its attached drive coupling 26 are moved into the recessed region 50 along the drive axis 22, until the drive coupling 26 and the drive shaft 18 extend through the centrally-located aperture 54 and an end of the motor 14 rests within the recessed region 50. A mounting fastener or fasteners 66 (FIG. 1) are then passed through the inner mounting apertures 58 of the motor mount 46 and into apertures 70 (e.g., threaded apertures) along the motor 14, to securely fasten the motor 14 to the motor mount 46.

With continued reference to FIGS. 1 and 2, in the illustrated example construction the rotary valve 10 further includes a proximal bearing cap 74, a set of spacers 78, and a set of proximal assembly fasteners 82. The proximal bearing cap 74 includes a centrally-located aperture 86, and mounting apertures 90 spaced circumferentially around the centrally-located aperture 86. Other constructions include various shapes and sizes for the proximal bearing cap 74 other than those illustrated. Different numbers and locations of apertures are also possible. In the illustrated construction, the spacers 78 each include an aperture 94 that extends through the spacer 78. The spacers 78 are arranged such that the apertures 94 of the spacers 78 align with the mounting apertures 90 on the proximal bearing cap 74, and with the outer mounting apertures 62 on the motor mount 46. The proximal assembly fasteners 82 are sized and shaped to extend through the outer mounting apertures 62 on the motor mount 46, through the apertures 94 of the spacers 78, and through the mounting apertures 90 on the proximal bearing cap 74, so as to secure the motor mount 46 to the proximal bearing cap 74.

With continued reference to FIGS. 1 and 2, the illustrated rotary valve 10 also includes a rotor housing 98 that includes a centrally-located aperture 102 extending axially through the rotor housing 98. The rotary valve 10 also includes a rotor 106 that is sized and shaped to be disposed within the centrally-located aperture 102. The rotary valve 10 further includes bearings 110 and pre-load elements 114 (for example, biasing elements) that are sized and shaped to generally extend around proximal and/or distal ends 118, 122, respectively, of the rotor 106. The bearing 110 and pre-load elements 114 facilitate alignment and rotation of the rotor 106 within the centrally-located aperture 102. For example, and with reference to FIG. 1, one or more of the bearings 110 and the pre-load elements 114 may be located within the centrally-located aperture 86 of the proximal bearing cap 74. Other constructions include types, numbers, and arrangements of the bearings 110 and/or the pre-load elements 114 different than those illustrated.

With reference to FIGS. 1 and 2, in the illustrated construction the proximal end 118 of the rotor 106 includes a single protruding portion 126 that is sized and shaped to be received within the gap 42 of the drive coupling 26, such that the drive coupling 26 is releasably coupled to the rotor 106 along the drive axis 22. Rotation of the drive shaft 18 and the drive coupling 26 and its two protruding portions 38 rotationally drives (imparts rotation to) the protruding portion 126 and the rotor 106 overall within the rotor housing 98. Other constructions include different releasable arrangements between the rotor 106 and the drive coupling 26 or motor 14 in general. In yet other constructions, the rotor 106 is fixed to the drive coupling 26 or to the motor 14 in general (for example, to the drive shaft 18).

As illustrated in FIG. 2, the rotor housing 98 includes a proximal end 130 and a distal end 134. The proximal end 130 includes mounting apertures 136 (for example, threaded apertures) that align with the mounting apertures 90 of the proximal bearing cap 74. The mounting apertures 136 also align with the apertures 94 of the spacers 78 and the outer mounting apertures 62 of the motor mount 46. Ends (for example, threaded ends) of the proximal assembly fasteners 82 may thus extend through the proximal bearing cap 74 and be fastened within the mounting apertures 136 at the proximal end 130 of the rotor housing 98 to secure the proximal bearing cap 74 to the rotor housing 98.

With continued reference to FIGS. 1 and 2, in the illustrated example the rotary valve 10 further includes a distal bearing cap 138 having a centrally-located aperture 142, and mounting apertures 146 that are spaced circumferentially around the centrally-located aperture 142. As illustrated in FIG. 1, the distal end 134 of the rotor housing 98 includes mounting apertures 150 (for example, threaded apertures) that align with the mounting apertures 146 of the distal bearing cap 138. The mounting apertures 150 are spaced circumferentially around the centrally-located aperture 102. The rotary valve 10 further includes distal assembly fasteners 154 that may be passed through the mounting apertures 146 of the distal bearing cap 138. Ends (for example, threaded ends) of the distal assembly fasteners 154 may extend through the distal bearing cap 138 and be fastened within the mounting apertures 150 at the distal end 134 of the rotor housing 98 to secure the distal bearing cap 138 to the rotor housing 98.

As illustrated in FIG. 2, one of the bearings 110 may additionally be sized and shaped so as to fit over the distal end 122 of the rotor 106, and be located and/or nested at least partially within a central recessed region 158 along a proximal side of the distal bearing cap 138. Other constructions of the distal bearing cap 138 include arrangements of recessed regions and/or apertures for securing the distal bearing cap 138 to the rotor housing 98 other than those illustrated.

Figure 5:
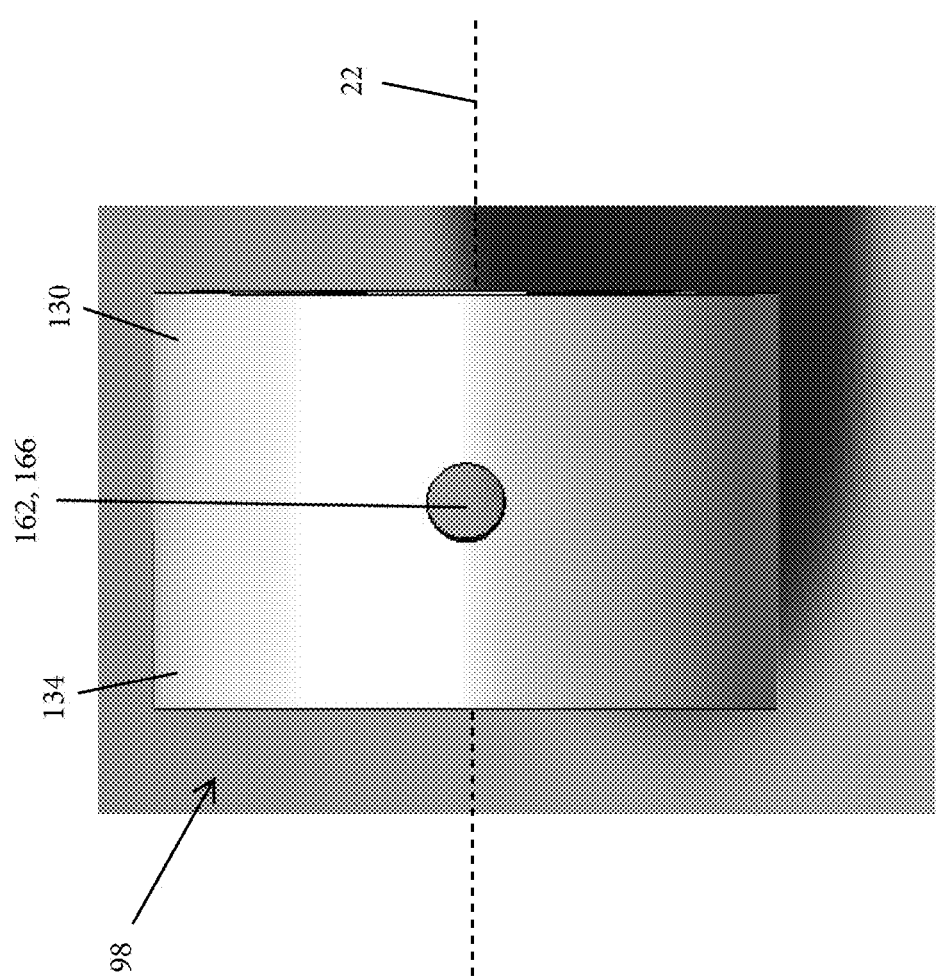
FIG. 5 illustrates a side view of the rotor housing.

FIGS. 3-11 illustrate additional details of certain embodiments of the rotor housing 98 and the rotor 106. With reference to the examples shown in FIGS. 3-5, the rotor housing 98 includes an inlet port 162 and an outlet port 166. In the illustrated example the inlet port 162 and the outlet port 166 are located on opposite sides of the rotor housing 98 (for example, 180 degrees apart around the drive axis 22), and are thus aligned with one another as seen in FIG. 5 along a direction perpendicular to the drive axis 22. In other constructions the inlet and outlet ports 162, 166 are located closer together, or are otherwise spaced differently than illustrated (for example, are not aligned as seen in FIG. 5). The inlet port 162 and the outlet port 166 each extend radially through a wall of the rotor housing 98, and are thus open both to the exterior of the rotor housing 98 and to the inner, centrally-located aperture 102. As described further herein, the inlet port 162 is sized and shaped such that compressed air (or other fluid) may enter the rotor housing 98 and pass into the centrally-located aperture 102. Similarly, the outlet port 166 is sized and shaped such that the compressed air (or other fluid) may exit from the centrally-located aperture 102 and out of the rotor housing 98.

Figure 6:
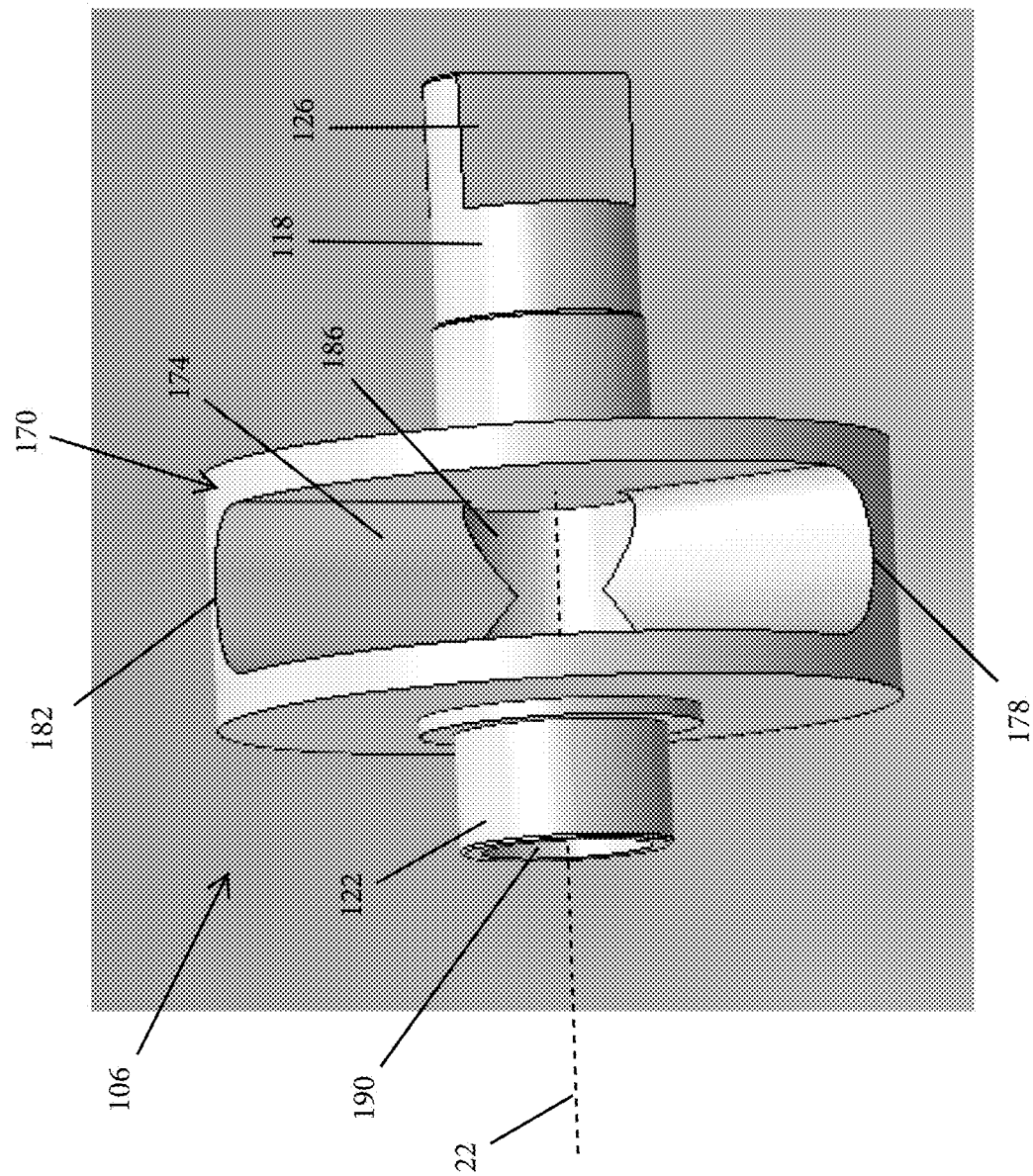
FIGS. 6-9 illustrate perspective views of the rotor.

With reference to FIGS. 6-9, the rotor 106 includes a main body 170 located between the proximal end 118 and the distal end 122. In the illustrated example construction, the main body 170 has a cylindrical, disk shape, although other constructions include different shapes than those illustrated. The main body 170 defines a dwell space 174. The dwell space 174 is, for example, a cut-out, or recessed region, extending radially inwardly, and circumferentially around a portion of the main body 170. With reference to FIG. 6, in the illustrated construction the dwell space 174 has a first end 178 and a second end 182 spaced circumferentially from the first end 178 less than 180 degrees around the main body 170 (e.g., 170 degrees, 160 degrees, 150 degrees, 140 degrees) relative to the drive axis 22. In some constructions, the first end 178 is spaced from the second end 182 by at least 180 degrees (e.g., 180 degrees, 190 degrees, 200 degrees, 210 degrees, 220 degrees). Other constructions include different spacing between the first end 178 and the second end 182. As is explained in more details below, in certain embodiments the dwell space 174 creates a pulsing action and movement of air to and from an instrument, and intermittently creates a pause of air movement toward or away from the instrument.

With reference to FIG. 6, at least a portion of the dwell space 174 extends radially inwardly to the drive axis 22, such that a portion of the drive axis 22 extends through the dwell space 174. As illustrated in FIG. 6, and in FIGS. 7 and 8, the dwell space 174 is defined by various surfaces along the main body 170, some of which intersect one another, particularly near the drive axis 22. In the illustrated construction these surfaces form a generally hour-glass shaped cut-out region 186 generally near the drive axis 22. Other constructions include various other shapes and surfaces that define the dwell space 174, including dwell spaces that are defined by one continuous surface (e.g., concave), or multiple surfaces that intersect.

Figure 7:
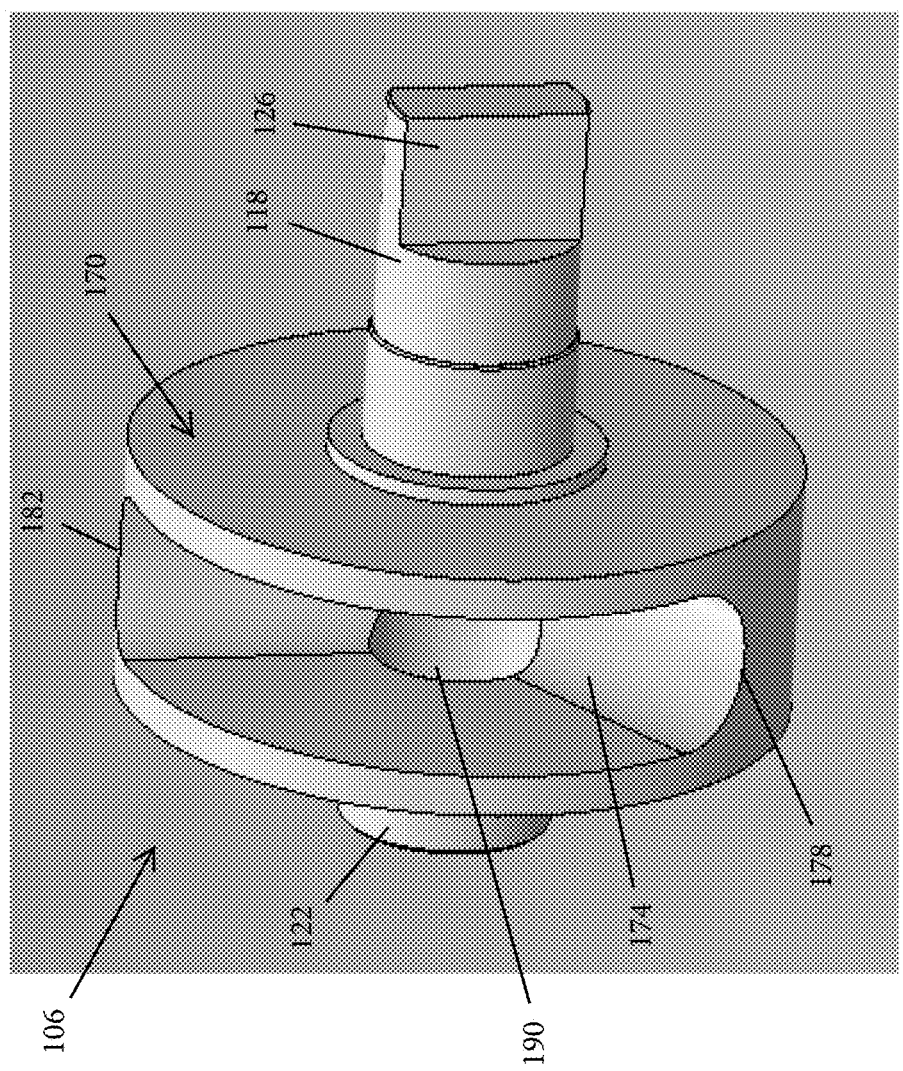
Figure 8:
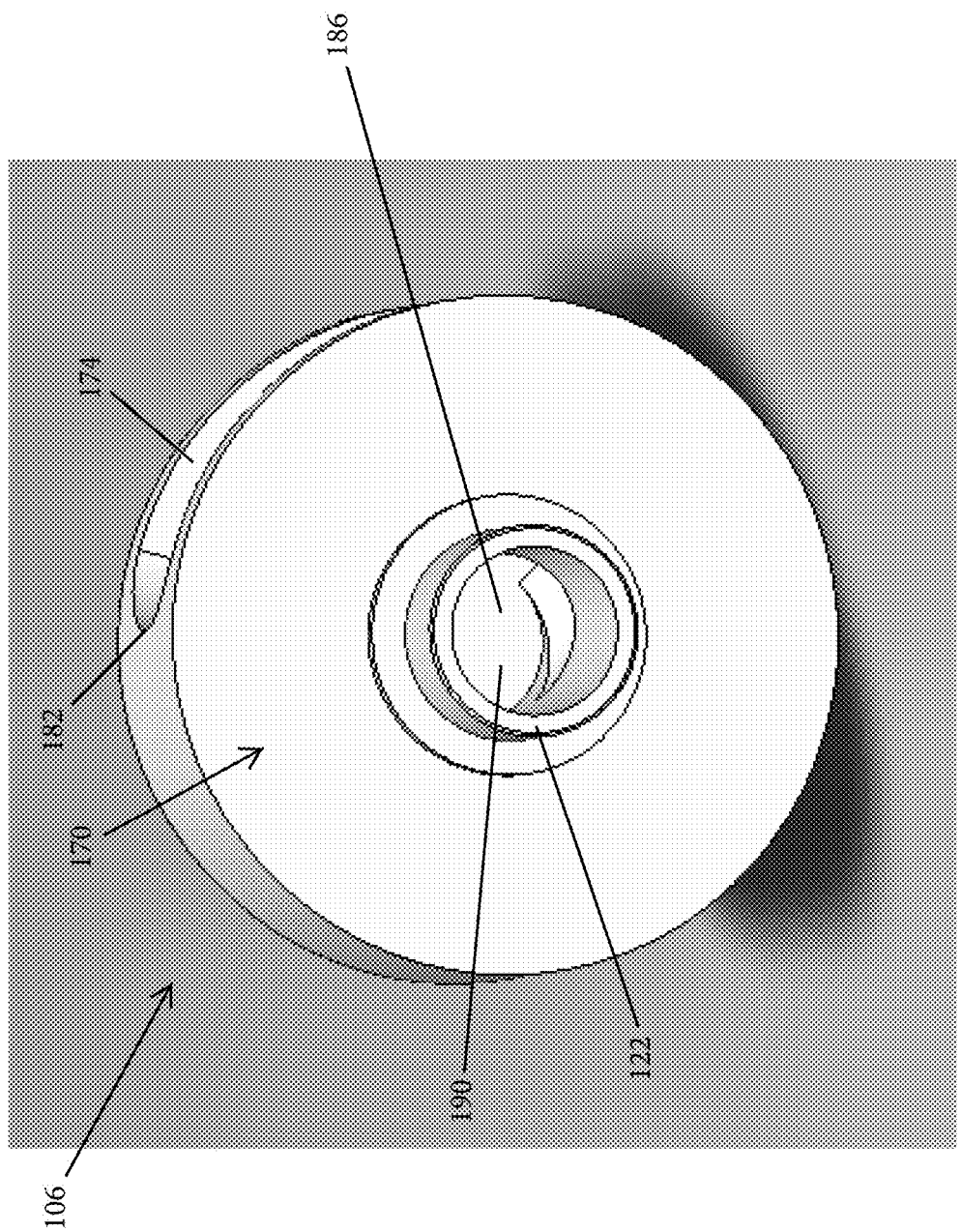
Figure 9:
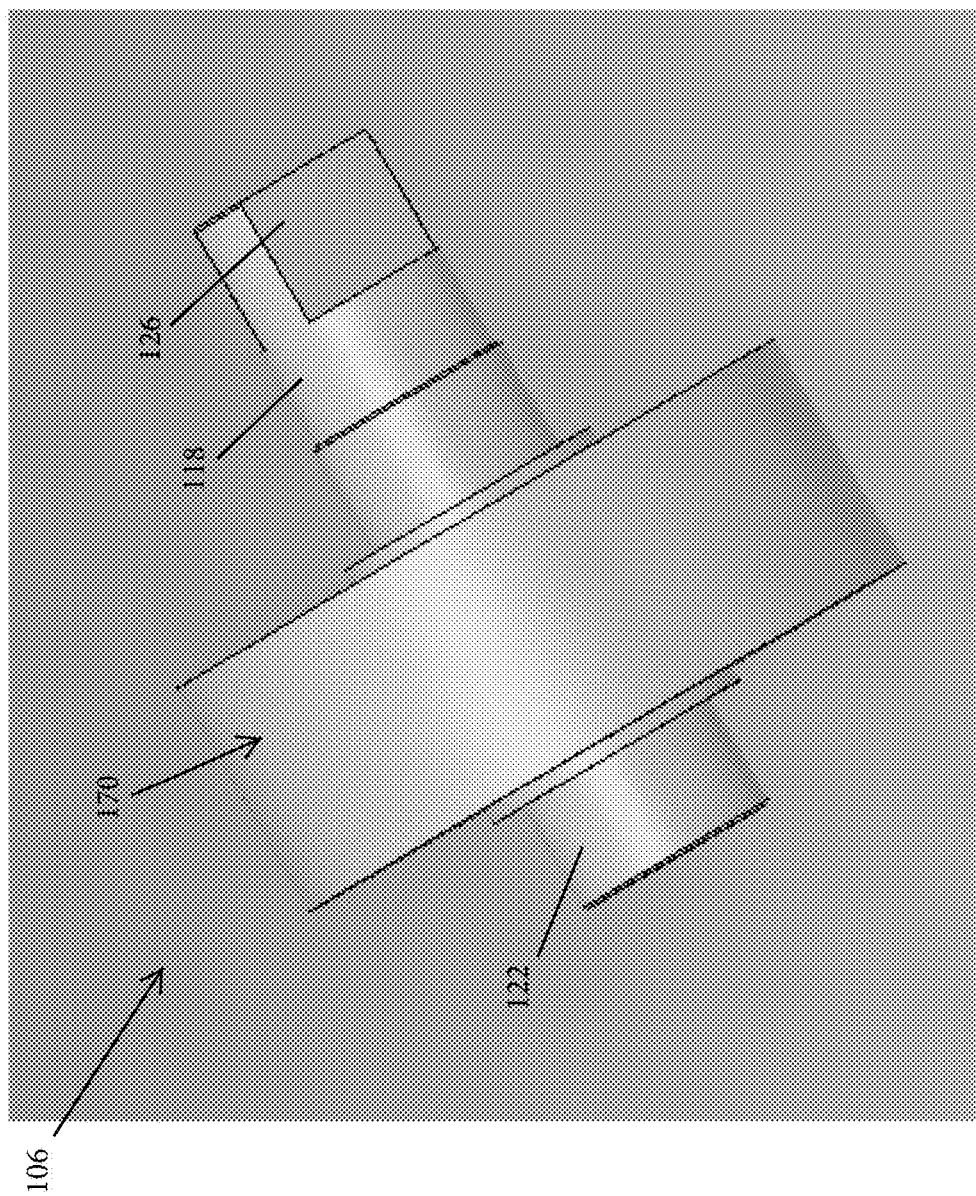

With reference to FIGS. 6-8, the distal end 122 of the rotor 106 includes a centrally-located aperture 190 that extends axially along the drive axis 22 through the distal end 122 and into the dwell space 174. In the illustrated example construction, the distal end 122 and the centrally-located aperture 190 are both cylindrical, although in other constructions the distal end 122 and/or the centrally-located aperture 190 may have other shapes (for example, oval, etc.). In the illustrated example construction, the cylindrically-shaped distal end 122 of the rotor 106 extends distally from the main body 170. As described further herein, the combination of the dwell space 174, along with the centrally-located aperture 190, provides a fluid pathway for fluid to both enter and exit the rotor 106.

Figure 3:
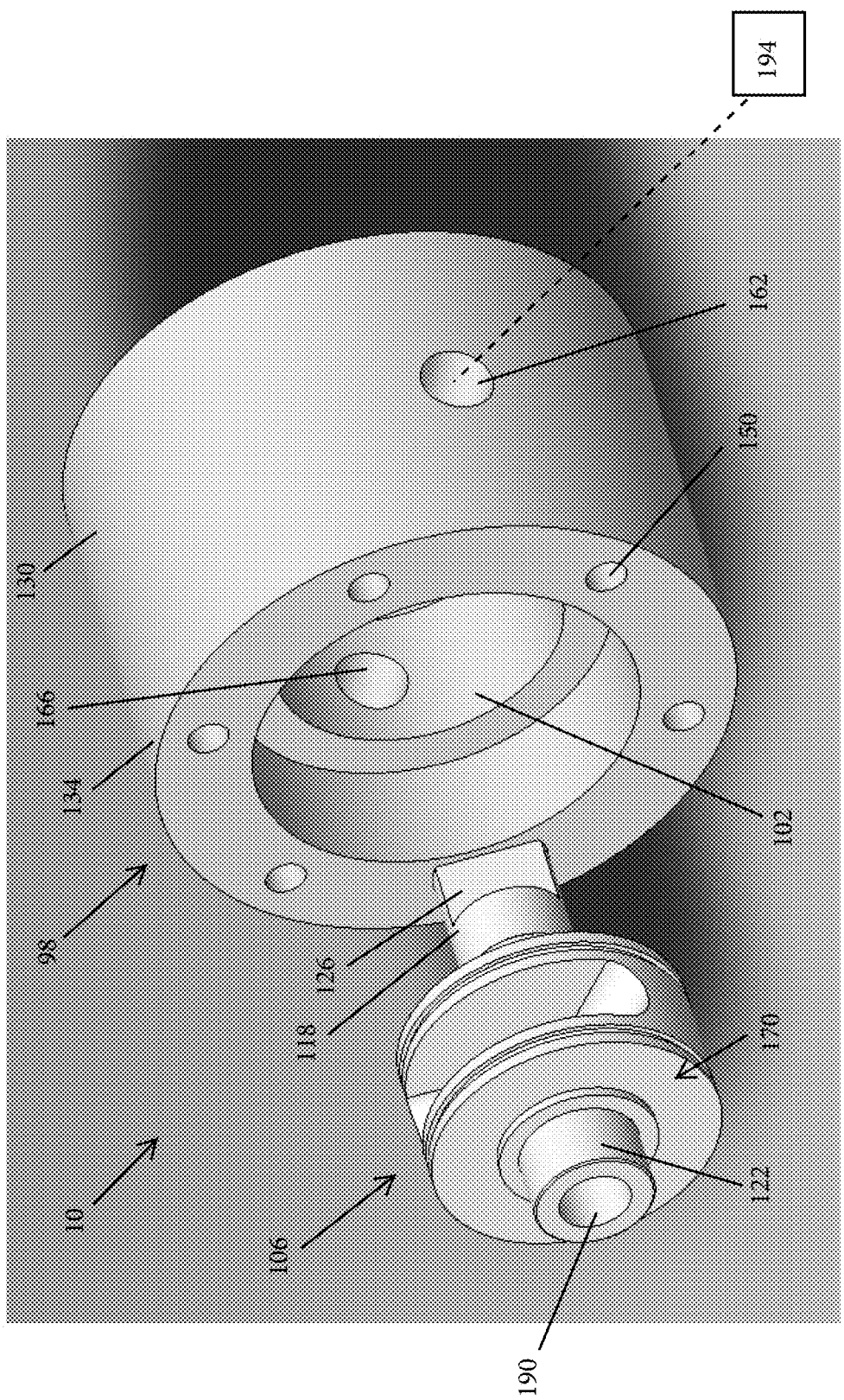
FIG. 3 illustrates a perspective view of a rotor housing and a rotor of the rotary valve.
Figure 4:
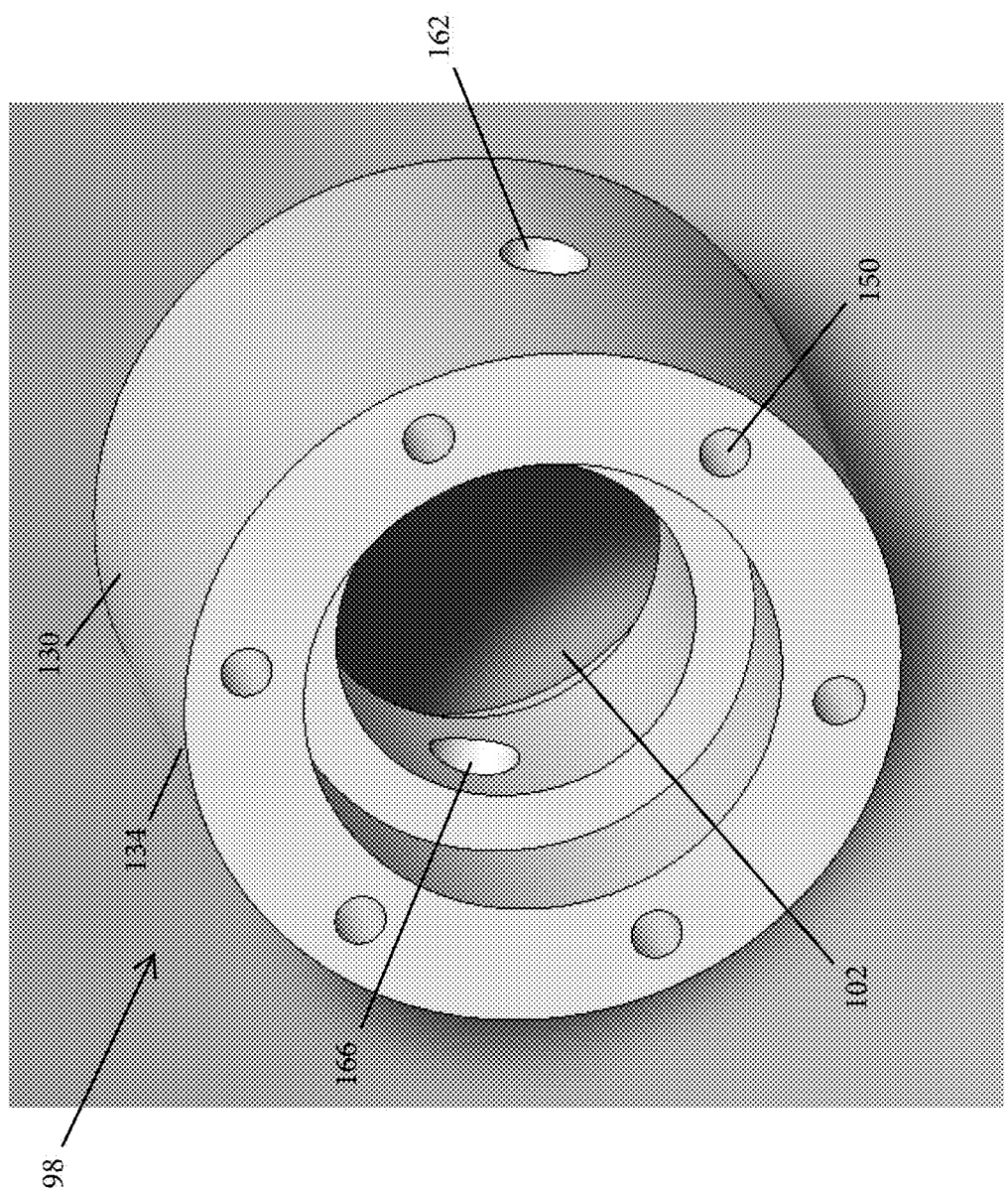
FIG. 4 illustrates a perspective view of the rotor housing.
Figure 10:
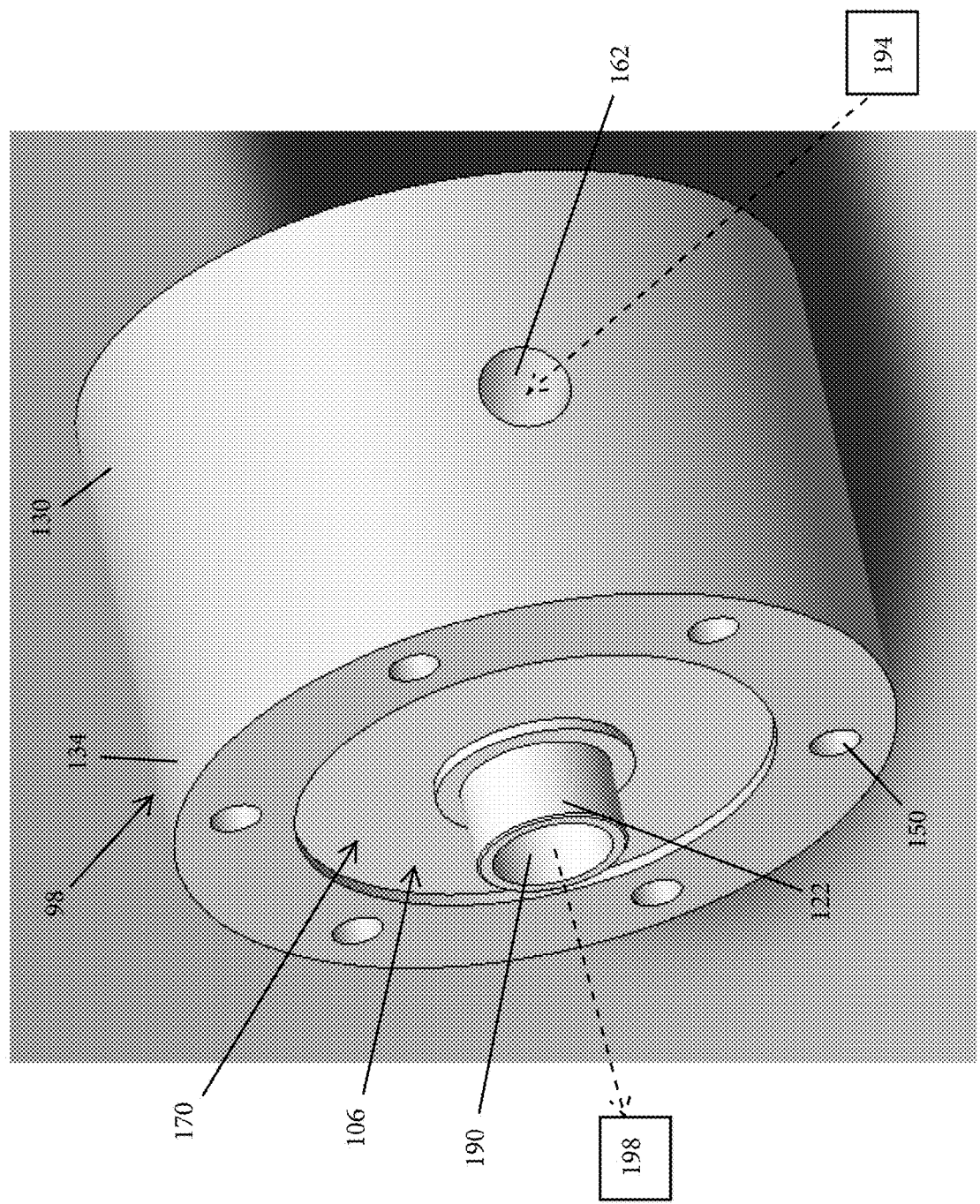
FIGS. 10 and 11 illustrate perspective views of the rotor being installed within the rotor housing.
Figure 11:
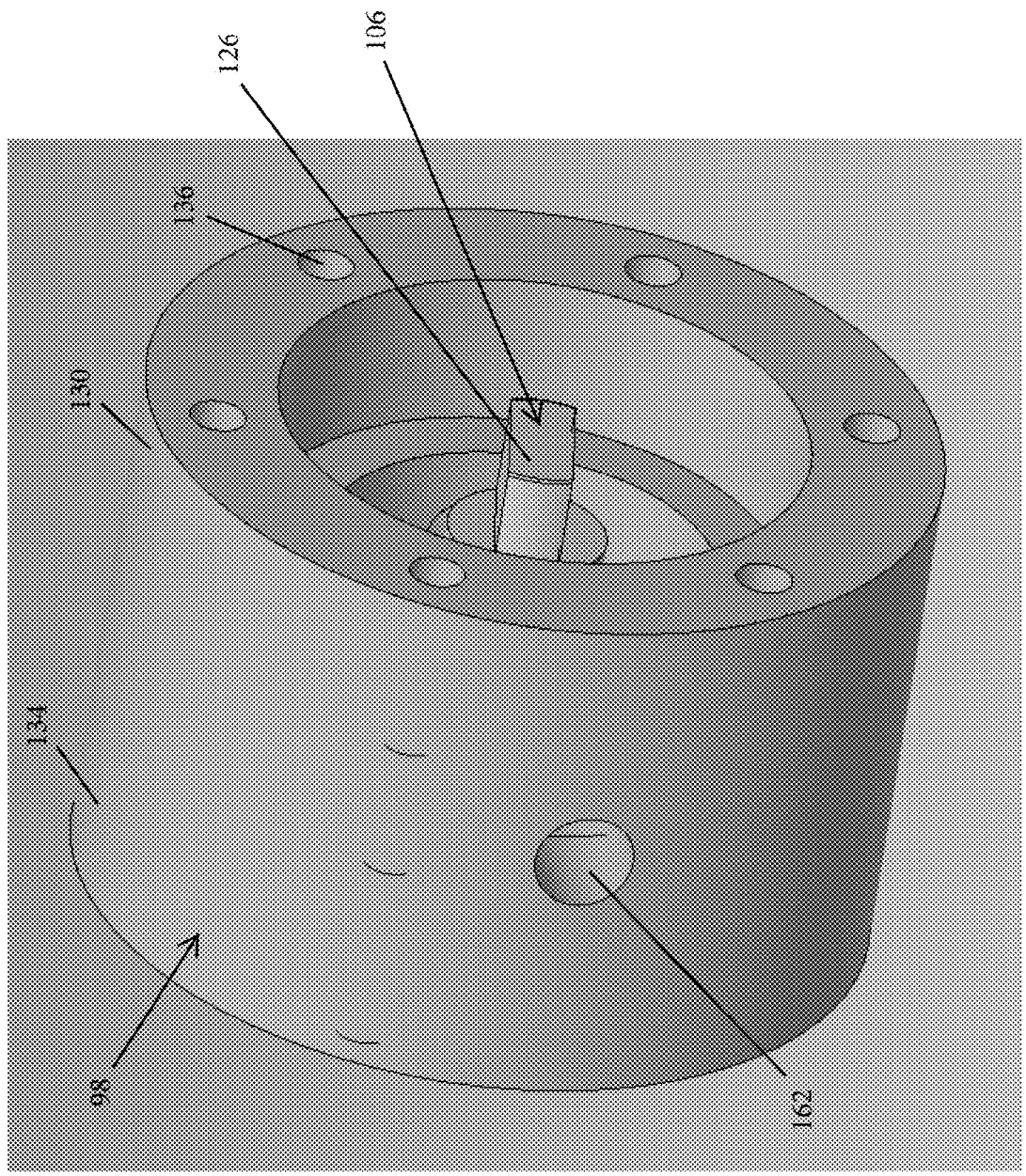

With reference to FIGS. 3, 10, and 11, and as described above, the rotor 106 is disposed within the centrally-located aperture 102 of the rotor housing 98. The rotor 106 is driven by the motor 14, and rotates within the rotor housing 98. As illustrated in FIG. 10, the inlet port 162 is coupled (for example, via a tube or other line, not illustrated) to a source 194 of compressed air (or other fluid). Rotor 106 is positioned within the rotor housing 98 such that the dwell space 174 rotates about the drive axis 22 when the motor 14 is activated. When the dwell space 174 (for example, the first or second end 178, 182 of the dwell space 174) reaches the inlet port 162, the compressed air from the source 194 may begin to enter through the inlet port 162, and into the dwell space 174. The compressed air travels radially through the dwell space 174, until the compressed air reaches the junction between the dwell space 174 and the centrally-located aperture 190. The compressed air then changes direction and travels axially through the centrally-located aperture 190, exiting out the distal end 122 of the rotor 106 (see arrows in FIG. 10). The compressed air then travels through the centrally-located aperture 142 of the distal bearing cap 138, and is directed to an instrument 198 (see FIG. 1), for example via a conduit (e.g., tube) coupled between the instrument 198 and the distal bearing cap 138. The instrument 198 may be, for example, an opthalmic instrument, such as a reciprocating cutter. In some constructions, the compressed air exiting the distal end 122 of the rotor 106 and passing through the distal bearing cap 138 to the instrument 198 is used to activate one or more bladders of a reciprocating cutting tool. In other constructions the compressed air may be directed to an instrument 198 other than a cutting tool.

With continued reference to FIG. 10, compressed air (or other fluid) may also travel back through the distal end 122 axially into the rotor 106 and into the dwell space 174. As the rotor 106 continues to turn, the dwell space 174 eventually reaches the outlet port 166 on the other side of the rotor 106. Once the dwell space 174 (e.g., the first or second end 178, 182 of the dwell space 174) reaches the outlet port 166, the compressed air may exit out of the rotor 106 and out of the rotor housing 98. Compressed air used to activate the instrument 198 may then return back through the centrally-located aperture 142 of the distal bearing cap 138, through the distal end 122 of the rotor 106 and into the dwell space 174. In some constructions, the air simply exits through the outlet port 166 into the environment around the rotor housing 98. In other constructions, a tube or other line is coupled to the outlet port 166 to deliver the air away from the rotor housing 98.

The rotor 106 is thus arranged to rotate continuously when the motor 14 is activated, accepting compressed air through the inlet port 162 when the dwell space 174 is aligned with the inlet port 162, and discharging compressed air when the dwell space 174 is aligned with the outlet port 166. In the illustrated example construction, the dwell space 174 may only be aligned with one of the inlet port 162 or the outlet port 166 at any given time. Thus, compressed air may not pass out of the rotor 106 and the rotor housing 98 when the dwell space 174 is aligned with the inlet port 162, and compressed air may not enter the rotor 106 and the rotor housing 98 when the dwell space 174 is aligned with the outlet port 166. This is due, for example, to the size of the dwell space 174 described above, and the circumferential distance between the first end 178 and the second end 182 of the dwell space 174. Because of this arrangement, the compressed air trying to enter the rotor 106 is momentarily stopped, or paused, as the rotor 106 and the dwell space 174 rotates. For example, when the dwell space 174 is not aligned with the inlet port 162, the rest of the rotor structure blocks movement of air through the inlet port 162 and into the rotor 106. When the dwell space 174 again rotates to a position where it is aligned with the inlet port 162, the air may then resume entering the rotor 106 and passing to the instrument 198. This cycle repeats, creating a pulsing movement of air to the instrument 198. Additionally, due to the size of the dwell space 174 and how far it extends circumferentially around the rotor 106, there may be a slight pause between the time when air is no longer able to pass through the inlet port 162 and into the dwell space 174 (i.e., when the dwell space 174 has rotated past the inlet port 162) and the time when the dwell space 174 rotates into a position where it becomes aligned with the outlet port 166 and where air may pass from the dwell space 174 and out the outlet port 166.

In other constructions, the rotor 106 includes a rotational position in which the dwell space 174 is aligned with both the inlet port 162 and the outlet port 166 (e.g., where the inlet port 162 is directing air into the dwell space 174 at the first end 178 of the dwell space 174, and where the outlet port 166 is directing air out of the dwell space 174 at the second end 182 of the dwell space 174). In such an arrangement, the rotor 106 still blocks movement of air through the inlet port 162 when the dwell space 174 is not aligned with the inlet port 162, and thus still creates a pulsing movement of air into the instrument 198 as the rotor 106 continuously rotates. However, during at least a portion of the time the dwell space 174 is aligned with the inlet port 162 air may be flowing both into the instrument 198 and/or out of the outlet port 166.

In certain embodiments, as the instrument 198 is driven faster and faster, and as the rotor 106 is driven faster and faster, the amount of time that the dwell space 174 is open to the inlet port 162 to receive compressed air during each revolution/cycle of the rotor 106 becomes less and less. At a given pressure, the reduction in the amount of time that the dwell space 174 is open to the inlet port 162 restricts the volume of air that enters the instrument 198 each cycle. To overcome this, some embodiments provide a rotor that includes more than one dwell space. For example, and with reference to FIG. 12, in some constructions a rotor 106' is provided that is similar to the rotor 106 described above, but includes two dwell spaces 174 in the main body 170. The dwell spaces 174 are aligned along the drive axis 22, and are fluidly connected along the drive axis 22, so that fluid (e.g., compressed air) may pass between the two dwell spaces 174 and through the centrally-located aperture 190 of the distal end 122 of the rotor 106'. In some constructions, compressed air travels radially through the inlet port 162 and then directly into one of the dwell spaces 174. A separate inlet port may be provided on the rotor housing 98. Compressed air may be passed through this separate inlet port into the other dwell space 174. Alternatively, a manifold or other structure may be used, so as to have a single, common inlet port that delivers compressed air or other fluid to both of the dwell spaces 174 in the rotor 106'.

Figure 12:
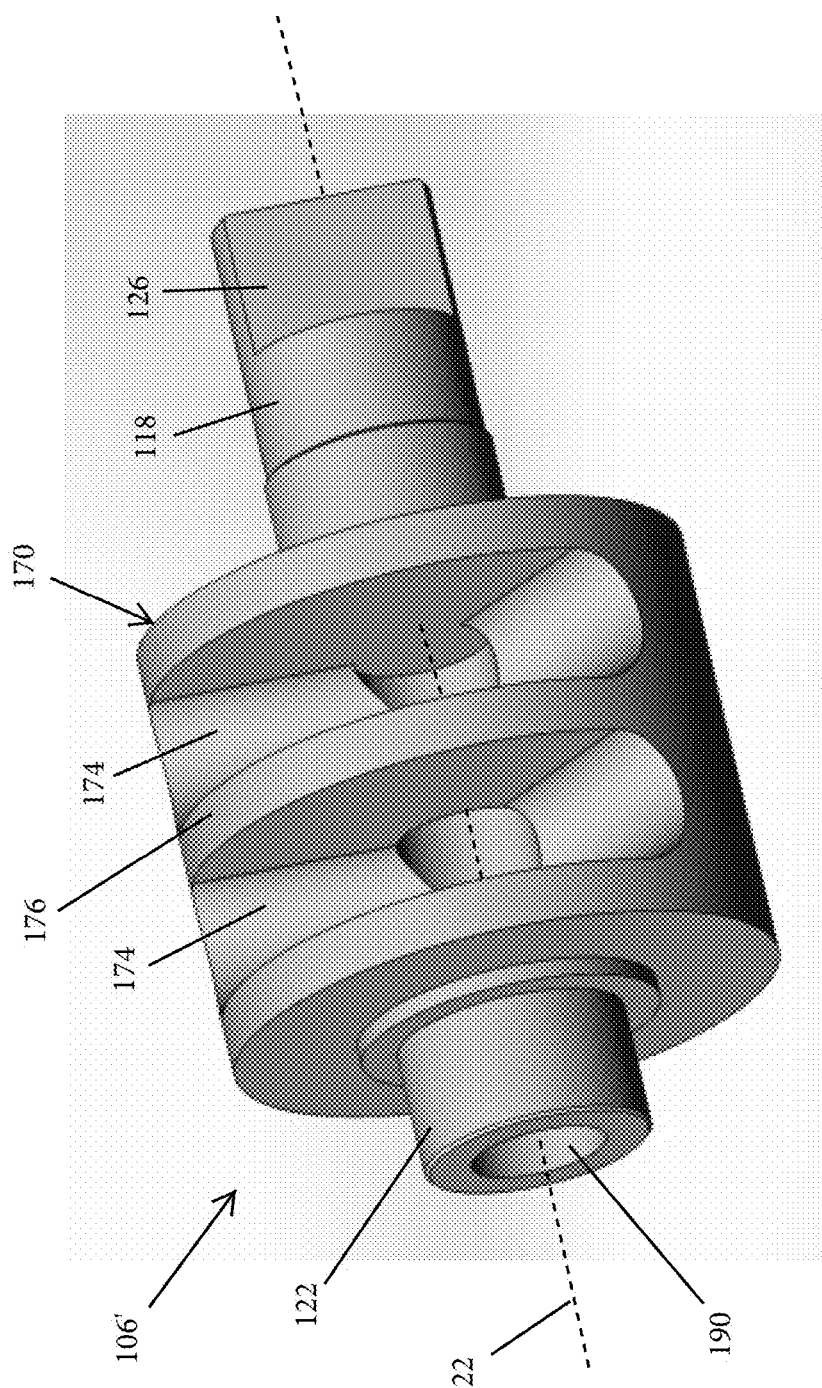
FIG. 12 illustrates a perspective view of a rotor according to another construction.

In the example illustrated, once the compressed air has been introduced into the dwell spaces 174, the compressed air travels radially inwardly through the dwell spaces 174 until it encounters the centrally-located aperture 190. The air then moves axially along the drive axis 22 out of the distal end 122 of the rotor 106', through the centrally-located aperture 142 of the distal bearing cap 138, and to the instrument 198. As illustrated in FIG. 12, a wall or rib 176 may separate a portion of the first dwell space 174 from a portion of the second dwell space 174. By using two dwell spaces 174 in this manner, more compressed air enters into the instrument 198 at the same given time and pressure. In other words, rather than increasing the pressure of the incoming compressed air to get more air into the instrument 198, the addition of an additional dwell space(s) 174 provides added air instead. Additionally, by incorporating more than one dwell space 174, the operating speed of the instrument 198 may also be increased, again without having to increase the pressure of the incoming compressed air.

Although various embodiments have been described in detail with reference to certain examples illustrated in the drawings, variations and modifications exist within the scope and spirit of one or more independent aspects described and illustrated.

What is claimed is:

1. A rotary valve comprising:
    a rotor housing having a first centrally-located aperture extending axially through the rotor housing, an inlet port, and an outlet port, wherein the inlet port and the outlet port each extend radially and open into the first centrally-located aperture; and
    a rotor configured to be disposed within the first centrally-located aperture, wherein the rotor includes a main body and surfaces on the main body that define a dwell space tapering radially inwardly from an exterior surface of the main body toward a drive axis of the main body, the dwell space extending circumferentially around a portion of the main body, wherein the rotor further includes a second centrally-located aperture that extends axially through a distal end of the rotor and intersects the dwell space within the main body, wherein the dwell space is sized and shaped to create a pulsing action and movement of air to and from a medical instrument.

2. The rotary valve of claim 1, wherein the dwell space has a first end located at the exterior surface of the main body, and a second end located at the exterior surface of the main body and spaced circumferentially from the first end less than 180 degrees around the main body.

3. The rotary valve of claim 1, wherein the rotor is configured to rotate about the drive axis, wherein the drive axis extends through the second centrally-located aperture and through a portion of the dwell space.

4. The rotary valve of claim 1, wherein the main body has a cylindrical, disk shape, and wherein the distal end of the rotor has a cylindrical shape extending distally from the main body.

5. The rotary valve of claim 1, wherein the rotor includes a proximal end and a distal end, wherein the main body is disposed between the proximal end and the distal end.

6. The rotary valve of claim 5, wherein the proximal end includes a protruding portion, and wherein the distal end is cylindrical and includes the second centrally-located aperture.

7. The rotary valve of claim 1, wherein the inlet port and the outlet port are spaced 180 degrees apart from one another around the rotor housing.

8. The rotary valve of claim 1, wherein the rotor housing includes a plurality of mounting apertures spaced circumferentially around the first centrally-located aperture.

9. The rotary valve of claim 1, wherein the inlet port and the dwell space are arranged such that when the rotor is disposed at a first rotational position within the rotor housing, compressed air passes through the inlet port, into the dwell space, and out the second centrally-located aperture.

10. The rotary valve of claim 9, wherein the outlet port and the dwell space are arranged such that when the rotor is disposed at a second rotational position within the rotor housing, compressed air passes through the second centrally-located aperture, into the dwell space, and out the outlet port.

11. The rotary valve of claim 1, wherein the rotor housing has a proximal end and a distal end, wherein the rotary valve includes a proximal bearing cap coupled to the proximal end of the rotor housing and a distal bearing cap coupled to the distal end of the rotor housing.

12. The rotary valve of claim 11, wherein the proximal bearing cap includes a third centrally-located aperture.

13. The rotary valve of claim 12, wherein the proximal bearing cap includes a plurality of mounting apertures spaced circumferentially around the third centrally-located aperture.

14. The rotary valve of claim 12, further comprising a motor having a drive shaft, and a drive coupling coupled to the drive shaft, wherein the drive coupling is configured to extend at least partially through the third centrally-located aperture.

15. The rotary valve of claim 14, wherein the drive coupling includes two protruding portions defining a gap therebetween, wherein the rotor includes a protruding portion at a proximal end of the rotor that is configured to extend into the gap, such that rotation of the drive shaft imparts a rotation of the rotor.

16. The rotary valve of claim 11, further comprising a motor mount and spacers, wherein the spacers are disposed between the motor mount and the proximal bearing cap.

17. The rotary valve of claim 16, wherein the motor mount includes a cylindrically-shaped recessed region, wherein the rotary valve includes a motor, and wherein a portion of the motor is configured to be disposed within the cylindrically-shaped recessed region.

18. The rotary valve of claim 1, wherein the rotor housing has a proximal end and a distal end, wherein the rotary valve further includes a distal bearing cap coupled to the distal end of the rotor housing, and an instrument coupled to the distal bearing cap, wherein the distal bearing cap includes a third centrally-located aperture that is aligned with the second centrally-located aperture of the rotor, wherein compressed air is configured to be directed out of the second centrally-located aperture of the rotor, through the third centrally-located aperture of the distal bearing cap, and to the instrument.

19. The rotary valve of claim 18, further comprising a plurality of mounting apertures spaced circumferentially around the third centrally-located aperture.

20. The rotary valve of claim 1, wherein the rotor includes a proximal end and a distal end, wherein the main body is disposed between the proximal end and the distal end, and wherein the rotary valve includes a first bearing positioned over the proximal end of the rotor and a second bearing positioned over the distal end of the rotor.

21. The rotary valve of claim 1, further comprising a motor having a drive shaft coupled to the rotor, wherein the drive shaft has a rotational speed of at least 40,000 revolutions per minute.

22. The rotary valve of claim 1, further comprising the medical instrument, wherein the medical instrument is a medical cutting instrument coupled to the rotary housing, wherein the dwell space is configured to create the pulsing action and movement of air to and from the medical cutting instrument.

23. The rotary valve of claim 1, wherein the dwell space is sized and shaped, and extends a circumferential distance around the rotor, such that during rotation of the rotor, a pause is configured to occur between a time when air is no longer able to pass through the inlet port and into the dwell space and a time when the dwell space has rotated into a position where the dwell space becomes aligned with the outlet port and where air is configured to pass from the dwell space and out the outlet port.

24. The rotary valve of claim 1, wherein the dwell space is the only dwell space within the main body.

25. A rotary valve comprising:
a rotor housing having a first centrally-located aperture extending axially through the rotor housing, an inlet port located on one side of the rotor housing, and an outlet port that is separate from the inlet port and is located on an opposite side of the rotor housing, wherein the inlet port and the outlet port each extend radially and open into the first centrally-located aperture, wherein the rotor housing has a proximal end and a distal end;
a rotor configured to be disposed within the first centrally-located aperture, wherein the rotor includes a main body and a dwell space extending radially inwardly into the main body and circumferentially around a portion of the main body, wherein the rotor further includes a second centrally-located aperture that extends axially through a distal end of the rotor and into the dwell space within the main body;
a proximal bearing cap coupled to the proximal end of the rotor housing and a distal bearing cap coupled to the distal end of the rotor housing, wherein the proximal bearing cap includes a third centrally-located aperture;
a motor having a drive shaft; and
a drive coupling coupled to the drive shaft, wherein the drive coupling is configured to extend at least partially through the third centrally-located aperture.

26. A rotary valve comprising:
a rotor housing having a first centrally-located aperture extending axially through the rotor housing along a first axis, an inlet port, and an outlet port, wherein the inlet port and the outlet port each extend radially and open into the first centrally-located aperture, wherein the rotor housing has a proximal end and a distal end spaced from the proximal end along the first axis;
a rotor configured to be disposed within the first centrally-located aperture, wherein the rotor includes a main body and a dwell space extending radially inwardly into the main body and circumferentially around a portion of the main body, wherein the rotor further includes a second centrally-located aperture that extends axially along the first axis through a distal end of the rotor and into the dwell space within the main body;
a proximal bearing cap coupled to the proximal end of the rotor housing;
a distal bearing cap coupled to the distal end of the rotor housing;
a motor mount having a set of first apertures; and
spacers disposed between the motor mount and the proximal bearing cap, wherein each of the spacers defines a second aperture extending entirely axially through the spacer along an axis that is parallel to the first axis, and wherein each of the second apertures is aligned with one of the first apertures.

27. The rotary valve of claim 1, wherein the inlet port is located on one side of the rotor housing, and the outlet port is separate from the inlet port and is located on an opposite side of the rotor housing.

28. The rotary valve of claim 1, wherein the rotor housing is a single piece housing.

29. The rotary valve of claim 25, wherein the rotor housing is a single piece housing.

* * * * *